[19] US009069095B1

(12) United States Patent
Beekman et al.

(10) Patent No.: US 9,069,095 B1
(45) Date of Patent: Jun. 30, 2015

(54) MONITORING THE OUTPUT OF A RADIATION GENERATOR

(71) Applicant: Schlumberger Technology Corporation, Sugar Land, TX (US)

(72) Inventors: Sicco Beekman, Houston, TX (US); Christian Stoller, Princeton Junction, NJ (US); Robert Arthur Adolph, Pennington, NJ (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 14/108,252

(22) Filed: Dec. 16, 2013

(51) Int. Cl.
G01D 18/00 (2006.01)
G01V 5/10 (2006.01)

(52) U.S. Cl.
CPC .......................................... *G01V 5/10* (2013.01)

(58) Field of Classification Search
CPC .......... G01V 5/102; G01V 5/108; G01T 3/00; G01N 2223/0745; G21G 4/02
USPC ...................................................... 250/252.1
See application file for complete search history.

(56) References Cited

U.S. PATENT DOCUMENTS

| 5,016,027 A * | 5/1991 | Uebbing ....................... 347/236 |
| 5,293,410 A | 3/1994 | Chen et al. |
| 6,754,586 B1 * | 6/2004 | Adolph et al. ..................... 702/8 |
| 6,884,994 B2 | 4/2005 | Simonetti et al. |
| 7,564,948 B2 | 7/2009 | Wraight et al. |
| 8,461,534 B1 | 6/2013 | Koltick |
| 2009/0057545 A1 | 3/2009 | Saenger et al. |
| 2009/0248309 A1 | 10/2009 | Neville et al. |
| 2011/0260044 A1 | 10/2011 | Wraight et al. |
| 2011/0313668 A1 * | 12/2011 | Thornton ........................ 702/8 |

FOREIGN PATENT DOCUMENTS

| WO | 2012162478 A2 | 11/2012 |
| WO | 2014059267 A1 | 4/2014 |

OTHER PUBLICATIONS

International Search Report and the Written Opinion for International Application No. PCT/US2014/070515 dated Mar. 16, 2015.

* cited by examiner

*Primary Examiner* — Kiho Kim
(74) *Attorney, Agent, or Firm* — Cathy Hewitt; Michael Dae (57) ABSTRACT

A method is described for obtaining an accurate and precise value for radiation output of a radiation generator. Radiation is generated in the radiation generator, and the radiation output of the radiation generator is measured using a radiation monitoring device. An instantaneous inferred radiation output is determined from operating parameters of the radiation generator, and over a period of time a calibration factor between the measured and the instantaneous inferred radiation output is determined. The accurate and precise value for radiation output is determined from the instantaneous inferred radiation output and the determined calibration factor.

20 Claims, 9 Drawing Sheets

MONITORING THE OUTPUT OF A RADIATION GENERATOR

FIELD OF THE DISCLOSURE

This disclosure is related to methods and devices for monitoring the output of a radiation generator such as pulsed or continuous neutron generator.

BACKGROUND

Many modern downhole logging tools use neutron generators. The neutron output of a typical generator may vary with time either through short term variations due to small instabilities in the neutron generation process, because of temperature variations or through longer term changes due to the aging of the generator, in general, and its vacuum tube, in particular.

Some downhole applications use radioisotopic neutron sources such as $^{241}$AmBe or $^{252}$Cf. For these sources, the changes of the neutron output are determined principally by the half-life of the parent radioisotope. Therefore, the change is predictable given that the decay or decay chain of the isotopes are known. It is therefore possible to use an initial calibration of the source strength and to predict the neutron output at a later time from it. Often, calibrations are repeated at regular intervals to keep track of the changes in neutron output, in particular for sources with a short half-life like $^{252}$Cf, which has a 2.6-year half-life.

For electronic neutron generators, be it CW generators of neutrons or pulsed neutron generators, the neutron output is less predictable due to the nature of the neutron generation process. Typically, neutrons are generated in a nuclear fusion reaction in a sealed vacuum tube, which is coupled to one or more high voltage sources. Ions are accelerated on a target in the vacuum tube and the energetic ions may fuse with nuclei of the target material, and this may lead to the generation of neutrons.

The principal interaction used in downhole logging is the fusion of a deuteron (deuterium nucleus) with a triton (tritium nucleus), which creates an alpha particle ($^4$He nucleus) and an energetic (14.1 MeV) neutron. In a typical generator tube, deuterium nuclei (d) or ionized deuterium molecules ($D_2^+$) are accelerated by high voltage potential differences of thirty kV to several hundred kV. The high acceleration voltage is required to impart the deuterium nucleus enough energy to overcome the Coulomb repulsion by the nucleus it is reacting with. The neutron output of a generator tube varies strongly with applied high voltage, internal gas pressure, target temperature and age to name a few. The neutron output may therefore change rapidly due to short term changes in the generator tube or the electronics controlling it. Such a change may be caused by parasitic electron emission in the tube due to the high electric fields or the interaction of the particle beam (d, T for example) with materials in the tube resulting in electron emission. Some events may lead to internal or external arcing and the neutron emission may cease almost entirely for short periods of time.

The neutron output of a neutron generator may be measured using a fast neutron detector in close proximity to the neutron source. Such a detector may be a plastic scintillation detector as described in U.S. Pat. No. 6,884,994, a solid state detector as described in U.S. patent application 2009/0057545, gas counter as indicated in U.S. patent publication 2011/0260044, all of which are assigned to the assignee of this disclosure, or another device that generates an output signal that is accurately related to the neutron output.

All of the above mentioned detectors rely on the detection of fast neutrons. Depending on the size and detection efficiency of the neutron monitor and the distance of the monitor from the source, the counting statistics in the neutron monitor may be low. In the absence of background subtraction, the uncertainty of a total number of counts is the square root of the number of counts. If a detector registers but 100 counts over a predetermined time period, the statistical uncertainty of the number of counts is ±10 counts (1 sigma). If precision of ±1% is required, 10,000 counts are desired and therefore an acquisition time larger by a factor of 100 is used.

In many cases, there is a desire to have a precise determination of the neutron output during a shorter time period and there is a desire for improving the precision over a shorter time period with a minimal impact on the accuracy of the neutron output measurement. Consequently, new developments in the field of output monitoring of radiation generators are desired.

SUMMARY

This disclosure is directed to a method for obtaining an accurate and precise value for radiation output of a radiation generator. Radiation is generated in the radiation generator, and the radiation output of the radiation generator is measured using a radiation monitoring device. An instantaneous inferred radiation output may be determined from operating parameters of the radiation generator, and over a period of time a calibration factor between the measured and the instantaneous inferred radiation output may be determined. The accurate and precise value for radiation output may be determined from the instantaneous inferred radiation output and the determined calibration factor.

Another aspect is directed to a method of operating a downhole tool in a borehole in a subsurface formation, the downhole tool comprising a radiation generator, an outgoing radiation monitor that operates during a first time interval but not during a second time interval, and at least one incoming radiation detector. The method may include generating radiation in the radiation generator, and measuring outgoing radiation from the radiation generator into subsurface formation using the outgoing radiation monitor during the first time interval. The method may further include determining an instantaneous inferred radiation output from operating parameters of the radiation generator during the first time interval, and determining a calibration factor between the measured and the instantaneous inferred radiation output. The method may also include determining the accurate and precise radiation output from the instantaneous inferred radiation output and the determined calibration factor, measuring incoming radiation from the subsurface formation using the at least one incoming radiation detector, and correlating the measured incoming radiation to the accurate and precise radiation output.

A device aspect is directed to a downhole tool having a neutron generator, and a neutron monitor to measure neutron output of the neutron generator. The tool may also have processing circuitry coupled to the neutron generator and neutron monitor. The processing circuitry may be configured to determine an instantaneous inferred neutron output from operating parameters of the neutron generator, determine over a period of time a calibration factor between the measured and the instantaneous inferred neutron output, and determine an accurate and precise neutron output from the instantaneous inferred neutron output and the determined calibration factor.

DETAILED DESCRIPTION

The present description is made with reference to the accompanying drawings, in which example embodiments are shown. However, many different embodiments may be used, and thus the description should not be construed as limited to the embodiments set forth herein. Rather, these embodiments are provided so that this disclosure will be thorough and complete.

In the following description the terms accurate and precise may be used. For the purpose of the present description, they are defined as follows:
- a precise measurement is a measurement with a small statistical error (good repeatability), but the average value may not coincide with the true value of the measured parameter, i.e., the true value of the parameter may be outside the statistical confidence interval of the measurement, and
- an accurate measurement refers to a measurement that provides the true value of a parameter, however, its statistical precision may be limited.

There is often a desire to know the neutron output of a neutron generator accurately over intervals as short as or less than 0.1 s and over periods of many hours or days. In order to obtain an accurate measurement of the neutron output, a neutron monitor may be used. A typical neutron monitor may be a detector of fast neutrons located close to the neutron generator in order to reduce fast neutron signals stemming from neutrons scattered in material surrounding the neutron source or the neutron instrument.

More specifically, such a neutron generator may be used in a downhole tool. The generator may be a pulsed neutron generator or a CW neutron generator, i.e., a neutron generator, in which the neutron output is continuous. In downhole applications, such a generator may be used in a wireline tool, a slickline tool, an LWD tool, a tubing conveyed tool or a permanent installation, for example.

An accurate and precise knowledge of the instantaneous neutron output of a generator is used to determine accurate neutron or gamma ray count rates in an instrument, which uses a neutron generator. Count rates in such an instrument are meaningful when the instantaneous source output is known. In the absence of an accurate knowledge of the neutron output, an instrument may have to rely on the use of ratios of count rates obtained by two or more detectors of incoming radiation in the tool during the same period of time.

A particular example of the desire for an accurate and precise neutron monitor measurement may be the accurate computation of a ratio of gamma ray counts in a neutron-gamma tool. The adjustment of the count rates for individual detectors to the correct depth is helpful to preserve accuracy in the face of layered formations, but brings challenges if the output changes while the tool is moving. The easiest way to be rigorous in the computation of a correct count rate ratio is to know the neutron output at the time each of the individual detector measurements was made. The time difference between measurements is of the order of seconds for normal logging speeds and detector spacings, making a very precise measurement very useful.

One possible neutron monitor may be a fast neutron detector using diamond as the detecting material. The use of diamond makes it possible to construct a compact rugged neutron detector. This is particularly useful in downhole tools, in which there is limited space for placing a neutron monitor. A typical detector may comprise a thin diamond wafer with an active area of about 0.25 cm$^2$ and a thickness of about 0.1 mm. Fast neutrons may interact with such a detector either through elastic scattering, causing carbon nuclei to recoil in the material or through nuclear reactions such as the reaction $^{12}C(n,n')3\alpha$ or $^{12}C(n,\alpha)^9Be$.

Figure 1:
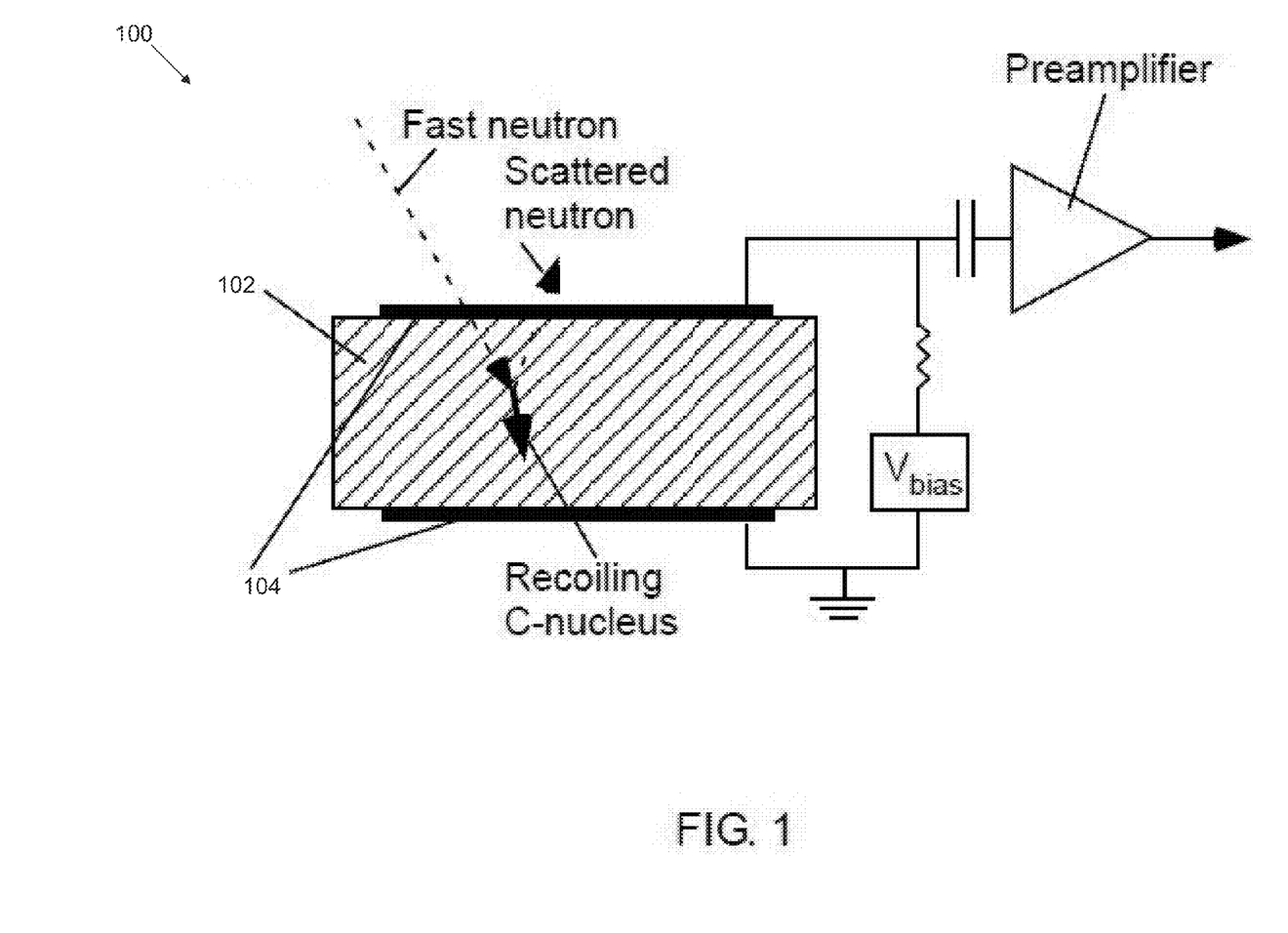
FIG. 1 shows a schematic drawing of a diamond detector used for the detection of fast neutrons.

FIG. 1 shows a schematic drawing of a diamond detector 100 and associated electronics used for the detection of fast neutrons. The detector 100 comprises a diamond wafer 102, with electrical contacts 104 on both sides. Fast neutrons entering the detector may scatter elastically or inelastically from carbon nuclei or may undergo nuclear reactions with carbon. The interaction may result in a carbon nucleus recoiling as shown in FIG. 1 or the reaction products from a nuclear reaction in the diamond may be stopped in the diamond. The charged particle interaction in the diamond may cause excitation of electrons to the valence band of diamond. If a potential of several 10 to several 100 V is applied between the electrodes 104 the electrons can travel to the positive electrode and the holes to the negative electrode causing a current pulse, the total charge of which may be related to the amount of energy deposited in the diamond.

Figure 2:
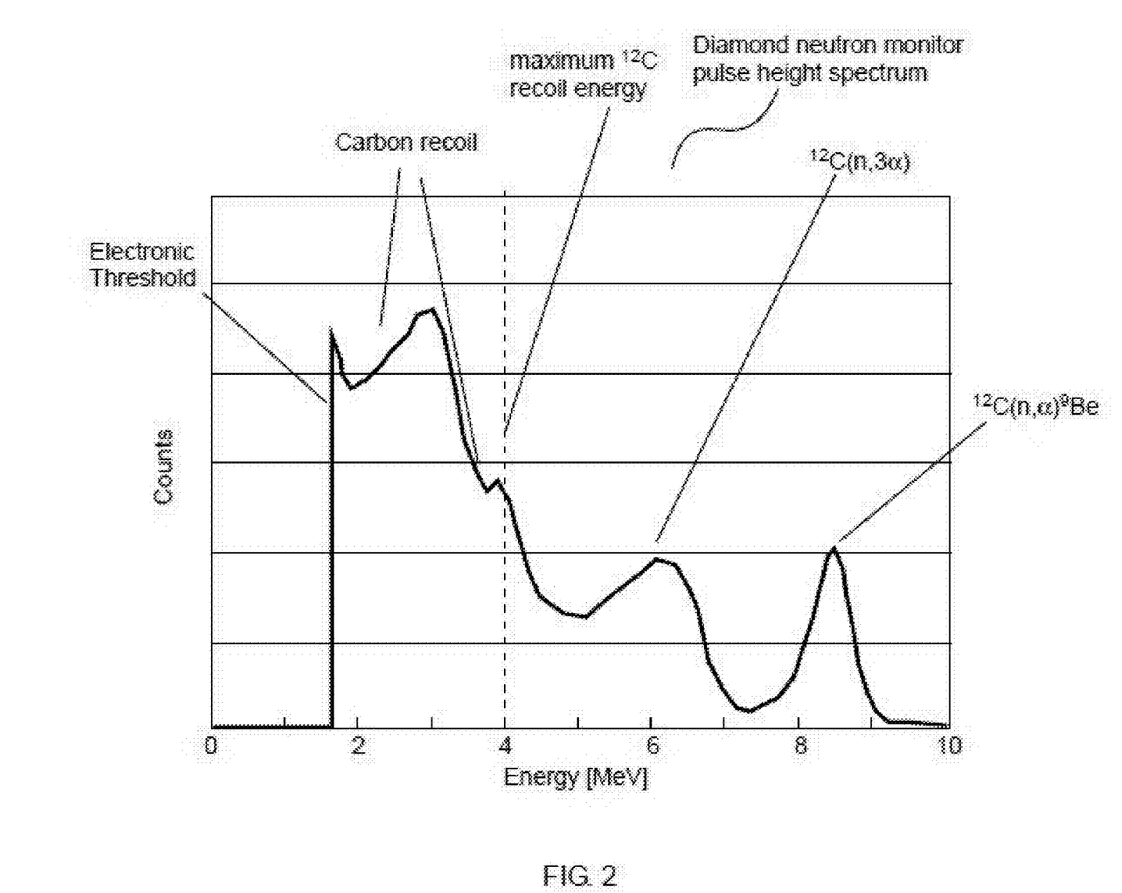
FIG. 2 shows the energy spectrum measured with such a detector exposed to 14.1-MeV neutrons from a d-T generator.

FIG. 2 shows the energy spectrum measured with such the diamond detector 100 of FIG. 1 exposed to 14.1-MeV neutrons from a d-T generator. Due to its low atomic number (Z=6), diamond has low gamma ray sensitivity. The spectrum in FIG. 2 shows that the energy deposition varies over a wide range. The displayed spectrum is starting at energy of about 2 MeV and the lower part of the spectrum has been suppressed. The spectrum shows features caused by the interaction of carbon recoiling after elastic scattering of 14-MeV neutrons creating recoil neutrons with energy up to 4 MeV, the $^{12}C(n,3\alpha)$ reaction and, at the highest energy, the peak from the $^{12}C(n,\alpha)^9Be$ reaction.

In a possible configuration, the detector may be exposed to a fast neutron flux of 14.1-MeV neutrons and may count 100 counts/s above the threshold indicated in FIG. 2. This means that the flux of neutrons is only known to ±10% for any 1-s interval.

Some applications may desire that the flux should be known to better than ±1%. However at 100 cps, as mentioned before, this involves integration over at least 100 s to obtain 10,000±100 counts or 100±1 cps precision. While the count rate of the monitor may be increased by using multiple detectors, thicker detectors or placing the detector closer to the source, this may not suffice to achieve the desired precision.

In some cases, the neutron monitor detector may be sensitive not just to the direct radiation from the neutron generator but may also be sensitive to gamma rays created in or around the tool. It may therefore be useful to account for such a signal to obtain an accurate neutron output measurement. This may be accomplished by increasing the energy threshold for the detected radiation in order to exclude most of the signals generated by gamma rays. Another possibility is to measure the signal in the monitor in the absence of the neutron burst, i.e., between neutron bursts and, in particular, directly after the neutron burst to infer the gamma ray contributions to the total signal, for example. This may be used to subtract a contribution, which is a function of the detected gamma rays after the burst, or to adjust the detection threshold to reduce or eliminate the parasitic contribution from gamma rays. It may also be possible to combine the two methods.

In yet another case, the neutron monitor may exhibit sensitivity to neutrons scattered back from materials surrounding the instrument. Such contributions may be accounted for by careful calibration of the instrument to quantify the contribution as a function of the environment so a correction can be applied or by using such calibration to determine an energy threshold for the detector signal above which such environmental contribution is insignificant. In yet another approach, the shape of the energy spectrum generated by the monitor detector may be used to detect spurious contributions and to eliminate them.

Figure 3:
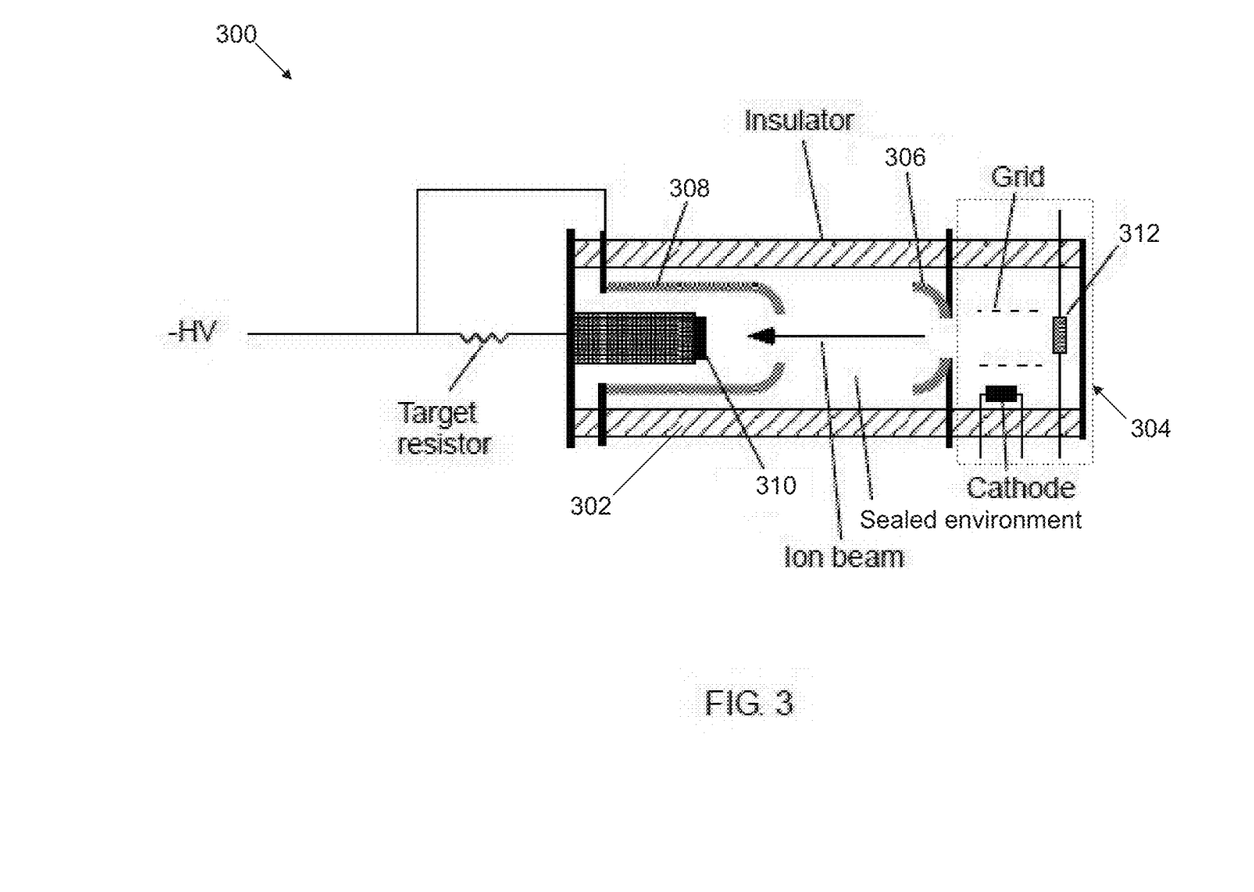
FIG. 3 shows a possible layout of a neutron generator tube.

The output of an electronic neutron generator may be inferred from its operating parameters. These parameters may comprise the beam current (current flowing from the ion source to the neutron tube target), the high voltage applied between the ion source and the target, the gas pressure in the generator tube and the temperature of the generator tube, in particular the target temperature, for example. A typical neutron generator tube 300 (see also U.S. Pat. No. 5,293,410) that may be comprised of a vacuum envelope 302, an ion source 304, an extractor electrode 306, a suppressor electrode 308 and a target (neutron source) 310 is shown in FIG. 3.

It may be possible to infer variations of the neutron output from one or more of the above parameters, the list of which is not exhaustive. For many parameters, there may be empirical relationships that relate them to the neutron output. Equation 1 gives an example of an equation that relates the beam current and the acceleration voltage to the neutron output:

$$N_{neutron} = c \cdot I_{beam} \cdot (V_{accel} - V_0)^2 \quad (1)$$

This means that the neutron output $N_{neutron}$ is proportional to the square of the acceleration potential $V_{accel}$ between ion source and the target minus a base voltage $V_0$ and directly proportional to the ion beam current $I_{beam}$. The two quantities can be measured with good precision in time intervals, which are smaller than 1 s and it is therefore possible to use them to infer the neutron output. As can be seen in FIG. 3 the voltage $V_{target}$ is not the same as the applied total voltage $V_{tot}$ in this example, since there is a voltage difference between the suppressor an the target due to the voltage drop dV in the target resistor $R_{target}$ and this voltage difference is a function of the beam current $I_{beam}$ as indicated in equation (2).

$$dV = I_{beam} \cdot R_{target} \quad (2)$$

The neutron output may drop with increasing target temperature. The target 310 temperature may be inferred from the external temperature at the tube 300, the power dissipation in the target for a given target material and the target construction and heat management. The target 310 may be a thin layer of titanium hydride for example.

The gas pressure in the generator tube 300 may be inferred from the heating current of the reservoir 312 (filament) and the temperature of the generator tube. In addition, ion source 304 parameters, such as the grid current and the grid acceleration voltage, such as the one shown schematically in FIG. 3, may impact the neutron output. Since the neutron generator tube 300 relies on complex mechanisms for the ionization of the gas, the acceleration of the ions and the fusion reaction in the target 310, the computed neutron output from available measured operational parameters may deviate from the measured output over extended periods of time, while accurately capturing output changes during shorter time intervals, where a short time interval may be of the order of seconds to hours. A neutron monitor may provide a precise measurement of the neutron output, i.e., a measurement with good statistical precision if the counts are accumulated over a sufficiently long time, and the accuracy of the answer, i.e., the accuracy of the neutron output with respect to a reference measurement (calibration), may be very good. Therefore it may be advantageous to use the accurate neutron monitor answer to recalibrate, from time to time or continuously, the neutron output inferred from the PNG operating parameters.

Figure 4:
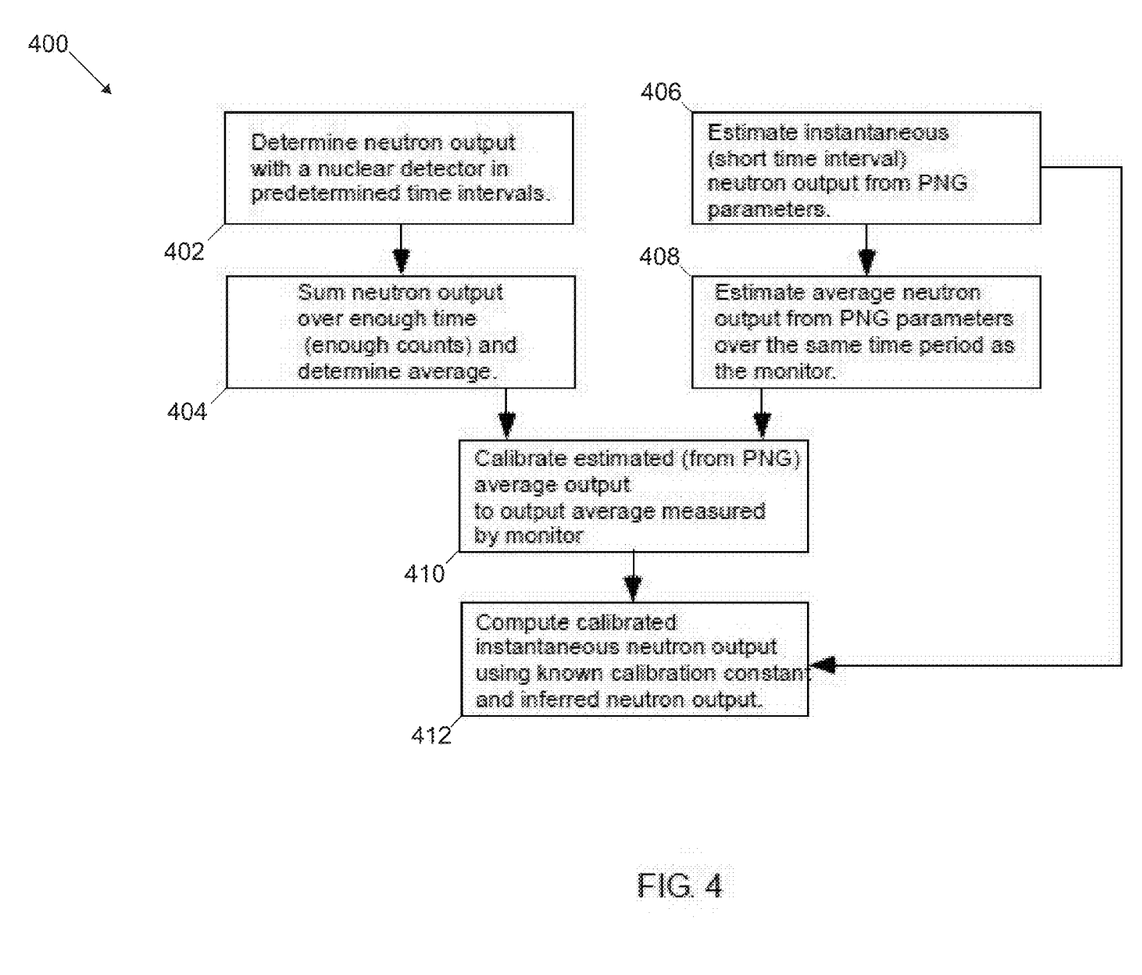
FIG. 4 shows a flow diagram of a possible calculation of the instantaneous neutron output.

A possible approach to such a recalibration is described in the flow diagram 400 in FIG. 4. The neutron monitor counts are measured over a predetermined time interval or until sufficient counts have been accumulated (402). At the end of the accumulation the average monitor count rate is determined (404). During the same time interval, a neutron output may be estimated from the neutron generator operating parameters (406) and its average over the time period may be computed at its end (408). The difference or the ratio for example between the measured and the inferred average neutron output may be used to calibrate the inferred neutron output (410). The calibration may be applied to the inferred instantaneous output to determine an accurate instantaneous neutron output or conversely an accurate inferred neutron monitor count or count rate (412).

The instantaneous output may be computed for the time interval, over which the average was computed provided the instantaneous estimated values have been stored and are available to be corrected. In some cases, the previous set of instantaneous estimated values may not be available or it may not be possible to delay the computation for the averaging time interval. In that case, the calibration factor or constant that has been determined in time interval $T_{-1}$ may be applied to the instantaneous values determined during the time subsequent interval $T_0$. In turn, the calibration determined during interval $T_0$ may be applied to the instantaneous estimated values during time $T_{+1}$ and so forth.

Figure 5:
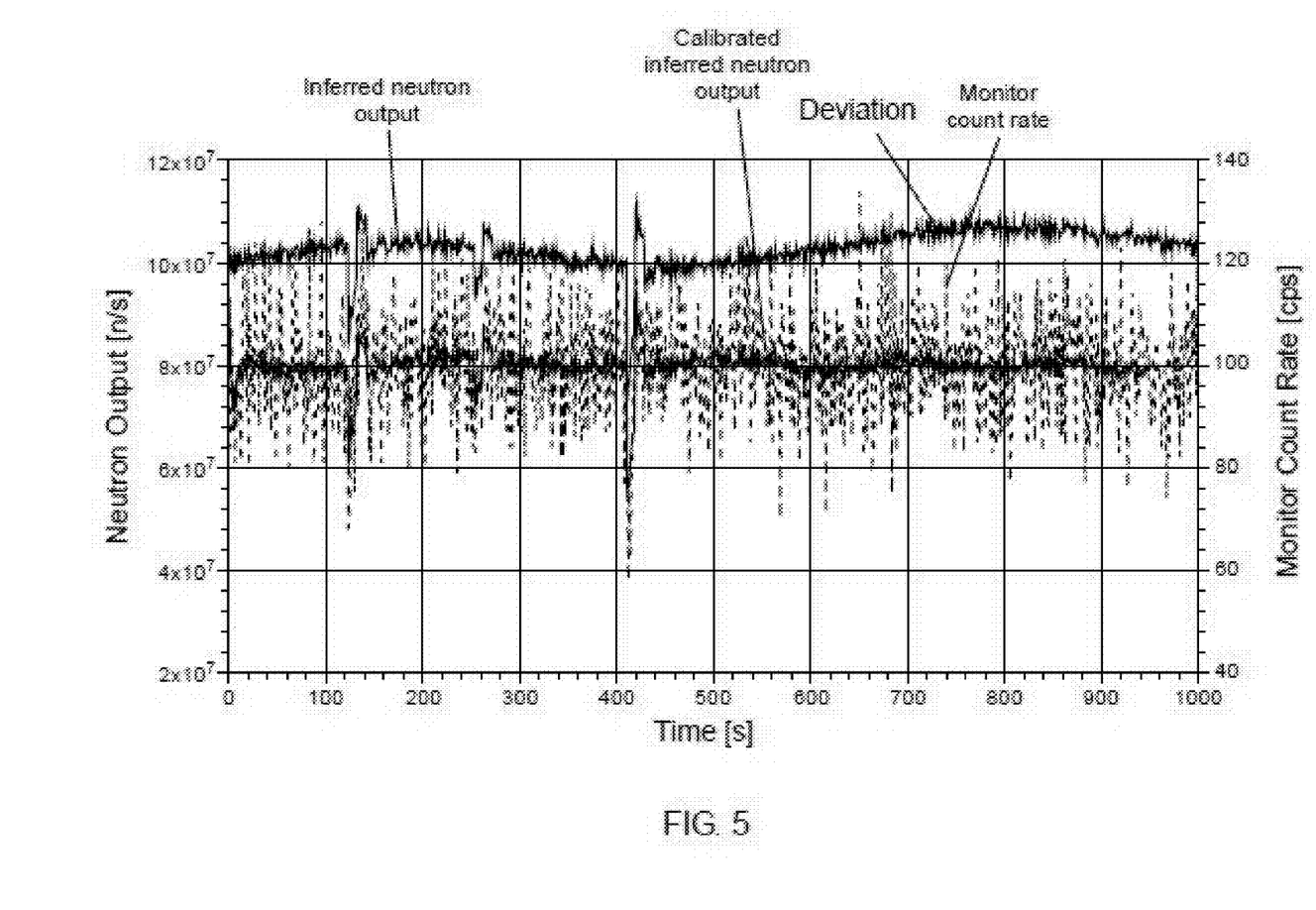
FIG. 5 shows an example of the method applied to a low count rate neutron monitor.
Figure 6:
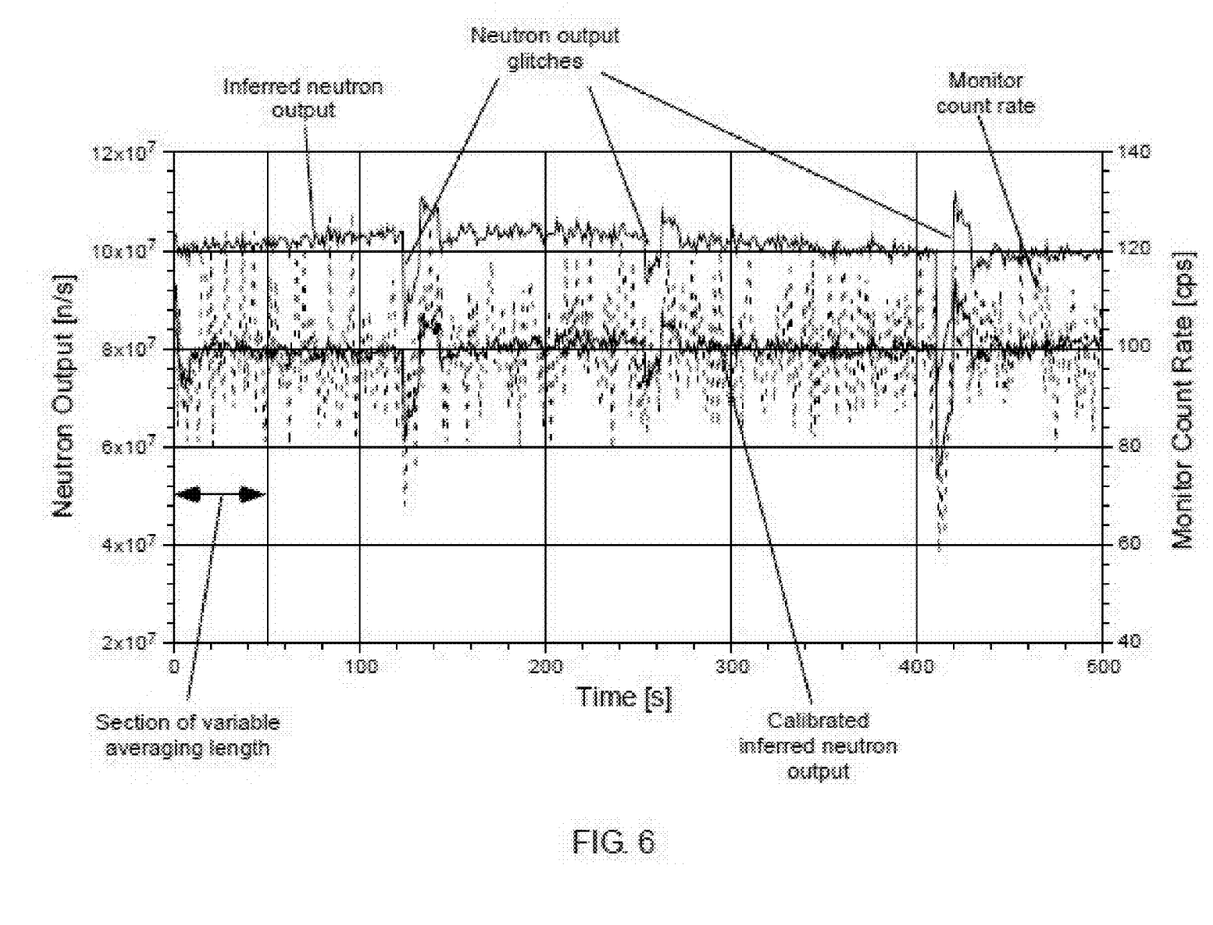
FIG. 6 shows details of the example in FIG. 5.

FIG. 5 shows a graph indicating the neutron monitor counts in 1-s intervals over a period of 1000 s together with the inferred neutron output over the same time interval. The inferred neutron output shows a slow variation and a small amount of noise in the 1-s samples. In this example, it is assumed that the neutron output is kept constant at $10^8$ n/s (neutrons/second) on average by using the neutron monitor. This may be achieved by regulating on an average neutron monitor count obtained over long periods of time or by using a regulation algorithm that is insensitive to the statistical nature of the monitor counts. In this example, the monitor count rate may be 100 cps on average for a neutron output of $10^8$ n/s. The monitor count rate is broadly scattered around the average value with a standard deviation of 10 cps following a Poisson distribution. Using sliding averages to recalibrate the inferred neutron output to the monitor count rate one may obtain the inferred neutron monitor count rate curve that passes through the middle of the neutron monitor counts. Since the recalibration is done over a long time interval, the glitches in the neutron output at about 130, 260 and 420 s are reflected accurately and at the same time, the slow deviation of the inferred neutron output from the average known output is removed. FIG. 6 shows details of FIG. 5, in particular, the behavior of the recalibration algorithm in the presence of rapid changes.

Figure 7:
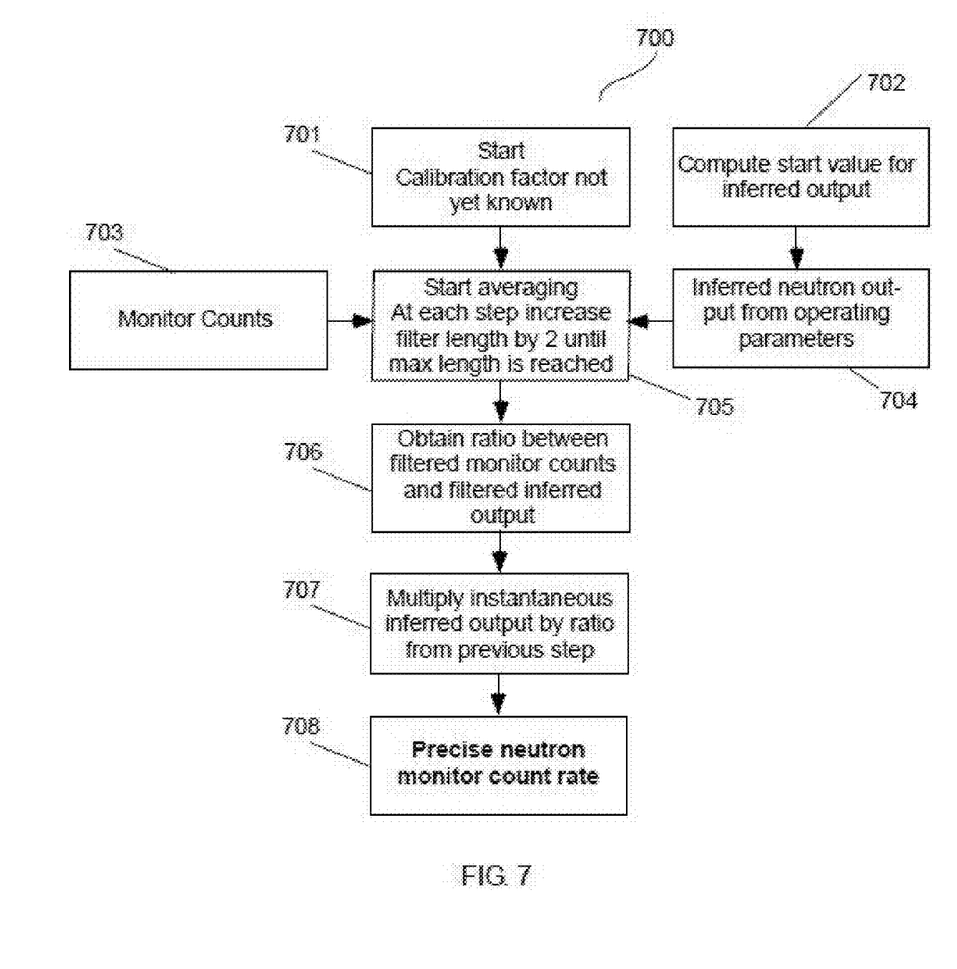
FIG. 7 shows a second flow diagram of a precise neutron monitor count rate computation.

FIG. 7 shows a diagram 700 of a possible dataflow for obtaining the calibration factor from the monitor counts and the inferred neutron output. In this embodiment, it is assumed that the calibration factor is unknown at the start as indicated in 701 and an initial value 702 for the inferred neutron is computed. The calibration factor may be established with increasing filter length for the monitor counts 703 and the inferred neutron output 704, until a predetermined filter length has been achieved. For the first period of time, which might be 1 second long, there may be the neutron monitor counts accumulated and the corresponding inferred neutron output obtained during the period of time to obtain the calibration factor, which may be computed as the ratio of the filtered counts and the filtered inferred neutron output. With every two additional 1-s intervals, the accumulation of counts and the averaging of the inferred neutron output may be extended 705 until the maximum predetermined filter length (99 intervals for example) or period of time is reached. The instantaneous precise neutron monitor count rate 708 may be computed as the product of the calibration factor and the instantaneous inferred neutron output 707. The calibration factor, which is the ratio of the filtered monitor counts and the filtered inferred neutron output 706, may be assigned as described in Table 1. As is shown, the filter length is 1 for interval 1, and then increases symmetrically around the interval for which the precise and accurate monitor output is computed until the desired filter length is reached. As indicated below, there may be instances, in which there is a rapid change in the calibration factor, which may necessitate a restart of the filtering.

In the above example, the instantaneous precise neutron output may be inferred after additional data have been acquired in subsequent time intervals, since the filter is assumed to be symmetrical and computation of the accurate and precise neutron output will lag the data acquisition. It should be noted that the filter length can be reduced in the same way as it is lengthened, if there is an indication that the calibration factor has changed suddenly for example. The calibration period may end at a time interval, at which a significant change is observed. Filtering may then resume from scratch after this interval, as indicated in box 701 in FIG. 7.

TABLE 1

A possible filtering approach

| Filter length | Intervals used | Interval, for which the computation is made |
|---|---|---|
| 1 | 1 | 1 |
| 3 | 1 to 3 | 2 |
| 5 | 1 to 5 | 3 |
| ... | | |
| 99 | 1 to 99 | 49 |
| 100 | 2 to 100 | 50 |
| ... | | |

The precise neutron monitor count rate may be obtained as described in the flow chart 700 of FIG. 7. It is assumed that initially there is no accurately known calibration factor between the monitor count rate and the inferred neutron output. One may therefore start by filtering over shorter intervals until a desired interval length has been reached. In the example of FIG. 5 and FIG. 6, the filter length is 99 samples.

The length may be an odd number to insure that the filter is centered around one point when using a symmetrical filter. For the first data point (monitor and inferred output) there is no filtering. For the second point, the filter uses three points symmetrical around point number 2. For the third point the filter has a length of 5 and is symmetrical around point 3. The filter length is increased until the maximum desired length is achieved. One has therefore the averages indicated in equations (1), for a filter length<desired length and equation (2) once the desired filter length is be used.

$$Mon_{average}(j) = \frac{1}{2j+1}\sum_{i=1}^{2j+1} Mon(i) \quad (1)$$

$$Mon_{average}(j) = \frac{1}{n}\sum_{i=j-n/2}^{2j+n/2} Mon(i) \quad (2)$$

where j is the channel in the center of the filter, n is the maximum filter length and $Mon_{average}(j)$ denotes the filtered neutron monitor count rate. The same averaging is done on the inferred neutron output Ninf to obtain the average $Ninf_{average}(j)$. The precise monitor count rate $Mon_{precise}$ may then be obtained according to equation (3).

$$Mon_{precise}(j) = Ninf_{instant}(j) \cdot \frac{Mon_{average}(j)}{Ninf_{average}(j)} = Ninf_{instant}(j) \cdot cal(j) \quad (3)$$

where cal(j) is the recalibration factor determined from the ratio between the monitor counts and the inferred output.

For the examples in FIG. 5 and FIG. 6, a simple box car filter was used, i.e., the average of the data points was computed over the length of the filter. Triangular filters or more complex filter functions may be used to e.g., increase the weight of the points that are close to the center of the filter, if the values at the center of the interval are to be compared.

In an alternate embodiment, a function may be fit to the data over a predetermined interval to obtain a more accurate representation of the calibration values. E.g., one may fit a low order polynomial to the data over the filter length n and one may use the value at the center of the fitting interval in lieu of the average of equations (1) and (2). The same fitting function may sometimes not be used for both variables. For example one may use a polynomial fit for the inferred neutron output to represent its slowly varying character, while using a straight average for the neutron monitor counts.

Figure 8:
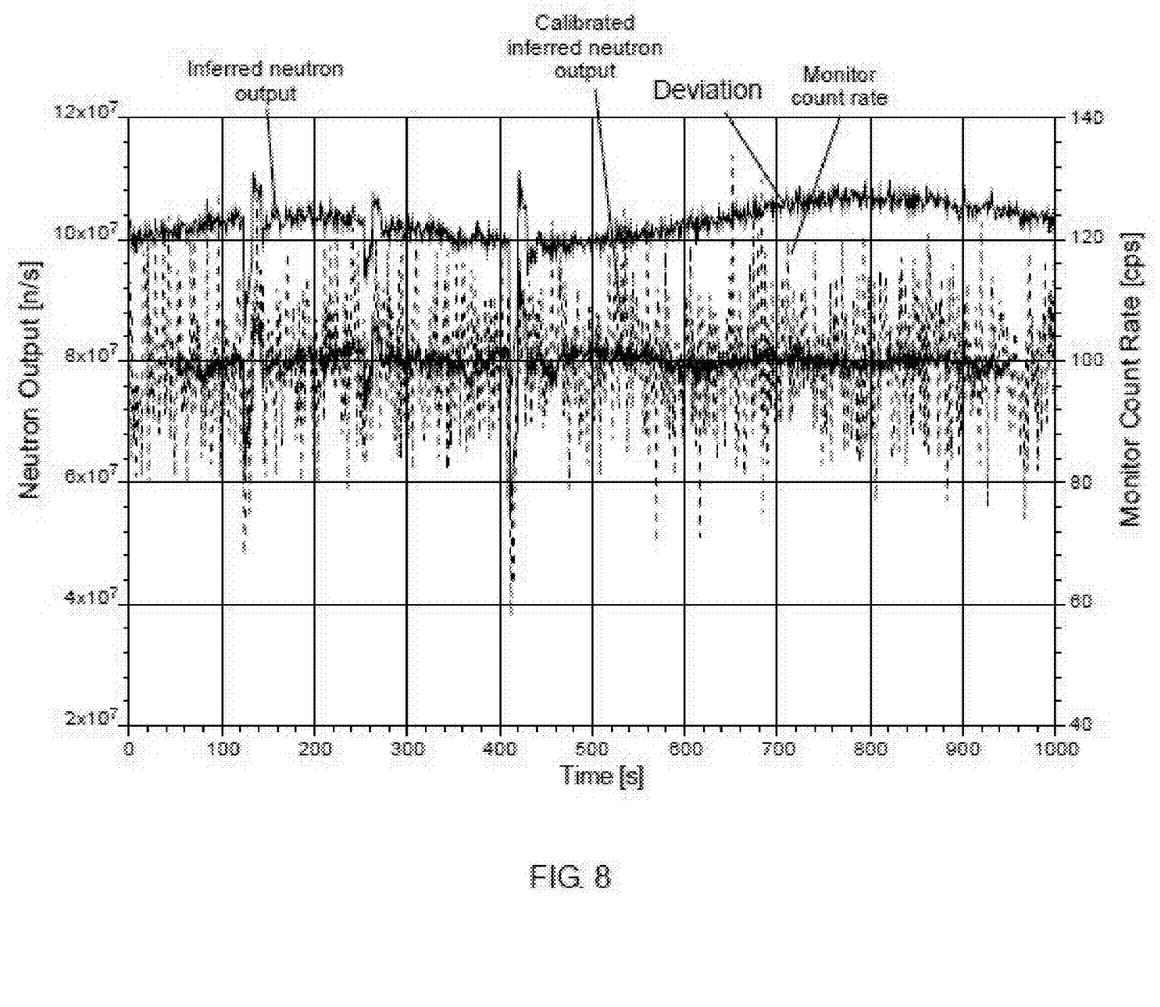
FIG. 8 shows an example of the method of the invention using a polynomial fit.

An example of such an approach is shown in FIG. 8. In this example, a polynomial fit was applied over 99 data points of the inferred neutron output and a box car filter (same as in FIG. 5 and FIG. 6) over the same length for the neutron monitor counts. The figure shows the inferred neutron output, the monitor counts and the derived precise monitor counts.

The above approaches may not be suitable in real time applications, where one may not want to delay computing an answer by more than 1 minute for example. In this case, one may still use an average as described above. However, one may use a trailing average as indicated in equations (4) and (5). In this case, one may average over a given length and use the average immediately for the calculation of the precise neutron monitor value. Like equation (1) equation (4) applies for the time period during which the filter length increases and equation (5) applies once the maximum filter length has been reached.

$$Mon_{average}(j) = \frac{1}{j}\sum_{i=1}^{j} Mon(i) \quad (4)$$

$$Mon_{average}(j) = \frac{1}{n}\sum_{i=j-n}^{j} Mon(i) \quad (5)$$

Figure 9:
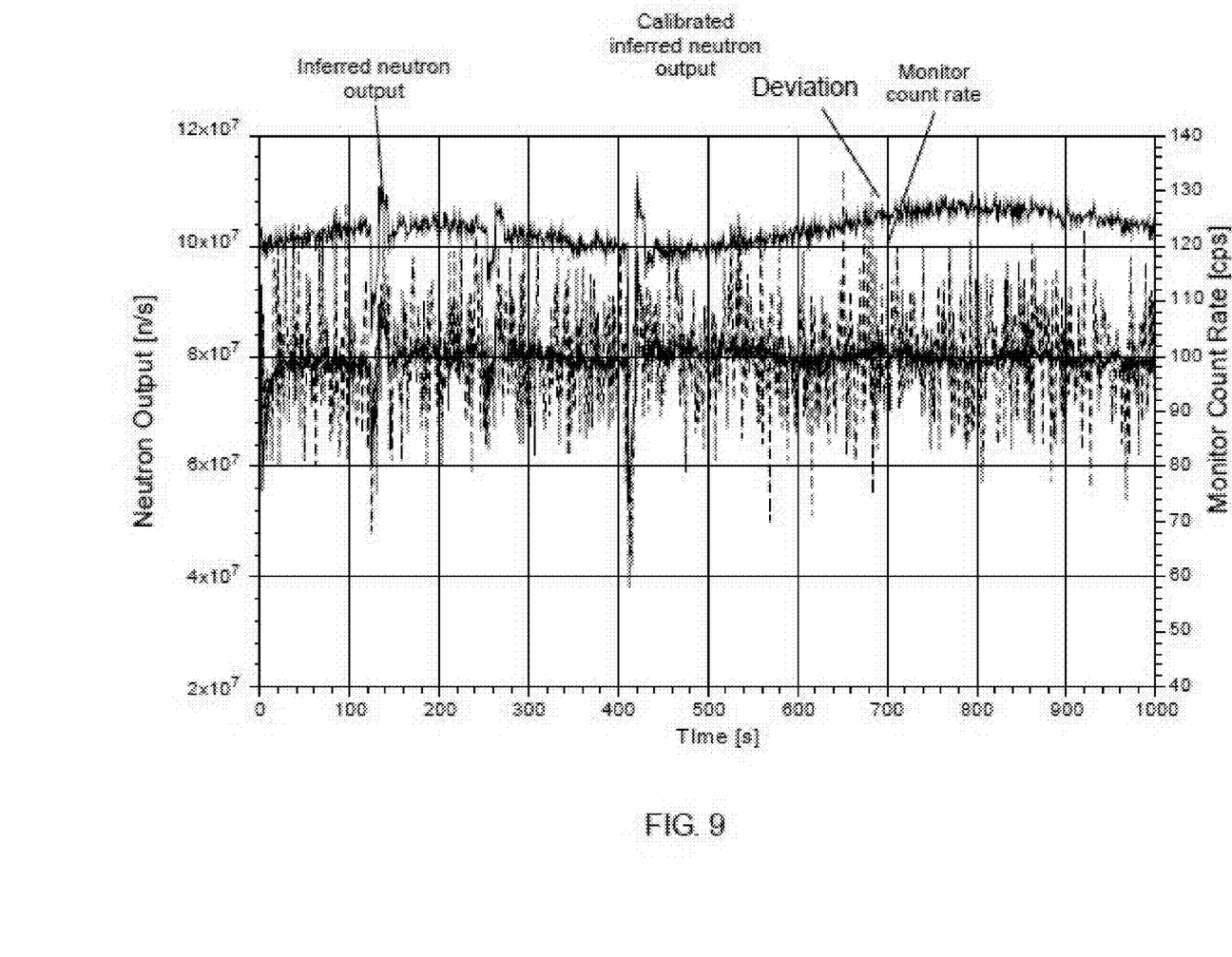
FIG. 9 shows an example of the method of the invention using a trailing filter.

If there is a substantial change in the inferred neutron output, this may lead to a small bias in the computed neutron monitor count rate. It may therefore be preferable to fit a linear function, a low order polynomial or another suitable function to the data in order to have a better representation of the drift of the inferred neutron output and, therefore a more accurate computation of the calibration factor between the monitor counts and the inferred neutron output. Application of a linear function may be done as indicated in equation (6)

$$Ninf_{linear}(n) = a_1 \cdot j + a_0 \quad (6)$$

where $a_0$ and $a_1$ are the coefficients of a linear fit to the neutron monitor count rates over the time interval of length j ending at point n. It should be noted that the midpoint of the fitting range will have a value corresponding to the average over the fitting range. An example is shown in FIG. 9. In this example a linear fit was used for the inferred neutron output and a box car average for the monitor. However, a linear fit may be used for both the monitor and the inferred output. The precise monitor output was obtained in the same way as indicated in equation (3) by replacing $Ninf_{average}$ by $Ninf_{linear}$.

More generally, the invention may be described as expressing the accurate and precise value of the neutron monitor counts $Mon_{precise}$ as a function of the monitor values $Mon(i)$ and precise inferred values $Ninf(j)$ over the same time interval as indicated in equation (7).

$$Mon_{precise}(i) = f(Mon(j), Ninf(k)) \quad (7)$$

where $Mon(j)$ indicates values obtained during a given period of time and $Ninf(k)$ indicates values obtained over the same period of time. However, the values of Mon and Ninf may or may not be obtained at the same frequency. Mon may be measured every 1 second while Ninf may be measured every 200 ms, for example.

While the above examples show a determination of a precise neutron monitor count rate derived from the accurate neutron monitor counts and the precise determination of the neutron output inferred from the operating and environmental parameters of the neutron generator, it is equally possible to derive an accurate inferred neutron output by calibrating the inferred output using the neutron monitor. This is indicated in equation (8).

$$Ninf_{accurate}(j) = Ninf_{instant}(j) \cdot \frac{Ninf_{average}(j)}{Mon_{average}(j)} \cdot Moncal \quad (8)$$

where Moncal is the known ratio between the neutron output and the monitor count rate. In the preceding examples, it is assumed that 100 cps in the monitor corresponds to $1 \times 10^8$ n/s.

While the periods of time, over which the accurate and the precise values, i.e., the monitor counts and the inferred neutron output, are determined should be overlapping or preferably be the same, the recalibration factor of equation (3) may be applied to an earlier or later interval. While the illustrative example above shows an inferred neutron output that deviated from the actual output over a period of 10 s of seconds, the inferred neutron output may be accurate over much longer periods of time. This makes it possible to determine the recalibration factor at longer time intervals.

In a different embodiment, the neutron monitor count rate may be translated into a measured neutron output by using a calibration factor relating the neutron counts to a neutron output. The same approach applies to the determination of the accurate and precise instantaneous output. Since the inferred and measured neutron output values will generally be similar, it may be possible to replace the ratio by an offset between the two values and the calibration factor becomes a calibration offset.

In a different embodiment, it may be possible to determine the neutron output and the recalibration factor during but parts of the measurement. This allows measurements to proceed even if the neutron monitor should be malfunctioning during some period of time, such malfunction may be a hardware failure, shock induced noise counts or a temporary malfunction induced by temperature as an example. In this case, the recalibration factor may be used together with the inferred neutron output to replace the monitor counts.

Should the monitor malfunction be temporary, as would be the case for shock induced noise or some temperature related issues, one may interpolate between the calibration factors before and after the malfunction to obtain an accurate neutron output in the interim.

The examples show that the inferred neutron output computation may be noisy. This noise can be reduced through the use filtering. It may be advantageous to use an adaptive filter, which reduces the filter length or stops filtering altogether if a fast transient is observed in the inferred neutron output. In this way, the precision may be improved without affecting accuracy in the presence of fast changes in neutron output, which may be caused by transients, such as electrical discharges in the generator or the generator tube. Alternatively, filtering periods may also be altered based on the detection of statistically significant changes in the neutron monitor measurement that are unaccompanied by changes in the operating parameters of the generator. Statistical tests can be used to determine when a change is statistically significant. This technique can be important when the neutron generator parameters are kept constant to keep a fixed output and an event occurs that does not change the inferred neutron output, but changes the real neutron output significantly (a leakage event is a prime example of this behavior).

It is also possible that inferred neutron output calculation may not be accurate in the presence of a large transient. In order to avoid biases to the average recalibration factor, the averaging or fitting of the data from the monitor and the inferred neutron output may be stopped over intervals, which show generator instabilities and the recalibration factor determined without the inclusion of transients may be applied to the entire interval.

While the method was presented by assuming that the two averages or other functions of the measured or inferred value may be determined independently, it is possible, as indicated also in equation (7) that an average or other suitable function may be determined by first taking the ratio (or other function of the two measurements) and then determining an average or other suitable function of the values derived from such a calculation.

While the method has been described with respect to a diamond-based fast neutron detector, the method applies to any detector that is capable of giving an accurate measurement of the fast neutron flux from the neutron generator. Such a detector may be a plastic scintillator coupled to a photomultiplier or other photon sensor, a silicon detector, a silicon carbide detector and a photon detector sensitive to inelastic gamma rays generated in the material in the direct vicinity of the pulsed neutron source, for example. In addition, a charged particle detector, such as a diamond detector, silicon detector, silicon carbide detector or other solid state detector lined with a layer of hydrogenous material, such as a layer of plastic, in which the recoil hydrogen nuclei (protons) are detected in the charged particle detector, may be used. The neutron monitor may also be a gas counter such as a $^4$He counter or a $H_2$-filled counter for example.

While the method has been described with respect to a neutron generator, other radiation generators such as x-ray generators may use similar approaches to improve the precision of the output measurement. An x-ray generator may comprise a DC x-ray generator, a Betatron or an electron Linac, for example. In this case, a radiation monitor sensitive to x-rays placed proximal to the radiation generator may be used to obtain a signal, which is proportional to the output of the x-ray generator as indicated in U.S. Pat. No 7,564,948.

The data processing may be done entirely by a processor in the downhole tool using a microprocessor, digital signal processor (DSP) or a field programmable gate array (FPGA) or a combination thereof for an example. Some or all of the data may be transmitted to a computer or processor at the surface, which may further process the data. The data transmission to the surface may be done through mud telemetry, wired drill pipe, electromagnetic transmission, wireline or fiber optic to name a few. The data at the surface may further be transmitted to other processors such as computers at a computing center, a client office, etc., by wired or wireless data transmission. Further data processing and analysis may be performed there on a single computer or multiple processors.

Data may be stored in the downhole tool, in particular if all the data cannot be transmitted to the surface in real time. The data may be stored in storage media such as flash memory, DRAM or SRAM. When the tool returns to surface the data may be transferred to a surface computer connected to one or more storage devices such as a magnetic hard drive, a solid state drive, DVD or CD, etc. The storage device may be attached to the surface computer or may be remote.

The data stored in the tool may be read out at surface or downhole and transferred to a processor for processing and analysis. Surface read out may be through a wired connection or wireless. Downhole read out may be obtained by coupling the downhole tool memory to a readout tool present in the hole, where such coupling may be wireless, wired or acoustic for example.

Many modifications and other embodiments will come to the mind of one skilled in the art having the benefit of the teachings presented in the foregoing descriptions and the associated drawings. Therefore, it is understood that various modifications and embodiments are intended to be included within the scope of the appended claims.

The invention claimed is:

1. A method for obtaining an accurate and precise value for radiation output of a radiation generator comprising:
   generating radiation in the radiation generator;
   measuring radiation output of the radiation generator using a radiation monitoring device;
   determining an instantaneous inferred radiation output from operating parameters of the radiation generator;
   determining over a period of time a calibration factor between the measured and the instantaneous inferred radiation output; and
   determining the accurate and precise value for radiation output from the instantaneous inferred radiation output and the determined calibration factor.

2. The method of claim 1, wherein the radiation generator is a neutron generator.

3. The method of claim 2, wherein the neutron generator is a pulsed neutron generator.

4. The method of claim 1, wherein the calibration factor is determined as a ratio of the measured radiation output averaged over the period of time and the instantaneous inferred radiation output averaged over the period of time.

5. The method of claim 4, further comprising determining the precise radiation output by multiplying the instantaneous inferred radiation output by the calibration factor.

6. The method of claim 1, wherein the calibration factor is associated with a middle of the period of time.

7. The method of claim 1, wherein the calibration factor is associated with an end of the period of time.

8. The method of claim 1, wherein the instantaneous inferred radiation output is determined during the period of time.

9. The method of claim 1, wherein the instantaneous inferred radiation output is not determined during the period of time.

10. The method of claim 1, wherein the calibration factor is determined for the end of the period of time by using a linear or a polynomial fit.

11. The method of claim 1, wherein the period of time is adapted dynamically based on changes in the operating parameters of the radiation generating device.

12. The method of claim 1, wherein the period of time is adapted dynamically based on statistically significant changes in the radiation output measured by the radiation monitor.

13. The method of claim 1, wherein the radiation generator operates during a first time interval but not during a second time interval; further comprising measuring background radiation during the second time interval; wherein the radiation output is measured during the first time interval; and further comprising correcting the radiation output based upon the measured background radiation.

14. A method of operating a downhole tool in a borehole in a subsurface formation, the downhole tool comprising a radiation generator, an outgoing radiation monitor that operates during a first time interval but not during a second time interval, and at least one incoming radiation detector, the method comprising:
   generating radiation in the radiation generator;
   measuring outgoing radiation from the radiation generator into subsurface formation using the outgoing radiation monitor during the first time interval;
   determining an instantaneous inferred radiation output from operating parameters of the radiation generator during the first time interval;
   determining a calibration factor between the measured and the instantaneous inferred radiation output;
   determining the accurate and precise radiation output from the instantaneous inferred radiation output and the determined calibration factor;
   measuring incoming radiation from the subsurface formation using the at least one incoming radiation detector; and
   correlating the measured incoming radiation to the accurate and precise radiation output.

15. The method of claim 14, wherein the accurate and precise radiation output is determined during a first time interval during which the outgoing radiation monitor operates.

16. The method of claim 15, wherein the accurate and precise radiation output is determined during the second time interval during which the outgoing radiation monitor does not operate.

17. A downhole tool comprising:
a neutron generator;
a neutron monitor to measure neutron output of the neutron generator;
processing circuitry coupled to the neutron generator and neutron monitor and configured to determine an instantaneous inferred neutron output from operating parameters of the neutron generator,
   determine over a period of time a calibration factor between the measured and the instantaneous inferred neutron output, and
   determine an accurate and precise neutron output from the instantaneous inferred neutron output and the determined calibration factor.

18. The downhole tool of claim 17, wherein the processing circuitry determines the calibration factor as a ratio of the measured radiation output averaged over the period of time and the instantaneous inferred radiation output averaged over the period of time; and wherein the processing circuitry averages the measured radiation output over the period of time.

19. The downhole tool of claim 17, wherein the processing circuitry averages the instantaneous inferred radiation output over the period of time and averages the measured radiation output over the period of time; wherein the processing circuitry determines a calibration factor as a ratio of the average measured radiation output and the average inferred radiation output; and wherein the processing circuitry determines the precise radiation output by multiplying the instantaneous inferred radiation output by the calibration factor.

20. The downhole tool of claim 17, wherein the downhole tool comprises a gamma ray detector coupled to the processing circuitry; wherein the neutron monitor operates during a first time interval but not during a second time interval; wherein the period of time, over which the calibration factor is determined, is the first time interval; wherein the processing circuitry measures incoming gamma rays using the gamma ray detector to determine a count rate; wherein the processing circuitry determines the accurate and precise neutron count during the second time interval; and wherein the processing circuitry correlates the count rate to the accurate and precise neutron output.

\* \* \* \* \*